United States Patent
Zhurba

(10) Patent No.: US 9,516,915 B2
(45) Date of Patent: Dec. 13, 2016

(54) FOOT PAD

(71) Applicant: Yuliya Zhurba, Chalfont, PA (US)

(72) Inventor: Yuliya Zhurba, Chalfont, PA (US)

(*) Notice: Subject to any disclaimer, the term of this patent is extended or adjusted under 35 U.S.C. 154(b) by 0 days.

(21) Appl. No.: 14/604,732

(22) Filed: Jan. 25, 2015

(65) Prior Publication Data

US 2016/0213093 A1    Jul. 28, 2016

(51) Int. Cl.
| | |
|---|---|
| A43B 7/26 | (2006.01) |
| A43B 3/12 | (2006.01) |
| A41B 11/00 | (2006.01) |
| A43B 17/00 | (2006.01) |
| A43B 3/00 | (2006.01) |

(52) U.S. Cl.
CPC ............ A43B 7/26 (2013.01); A41B 11/004 (2013.01); A43B 3/126 (2013.01); A43B 3/0078 (2013.01); A43B 17/006 (2013.01)

(58) Field of Classification Search
CPC .......... A43B 5/12; A43B 3/12; A43B 3/105; A43B 3/126; A43B 7/26; A43B 11/004; A41D 17/02
USPC ........................................................ 602/41
See application file for complete search history.

(56) References Cited

U.S. PATENT DOCUMENTS

| | | | |
|---|---|---|---|
| 1,867,679 A * | 7/1932 | Riehle | A43B 7/26 36/11.5 |
| 2,335,665 A | 11/1943 | Goldmerstein | |
| 2,497,528 A | 2/1950 | Baker | |
| 2,543,272 A | 6/1950 | Beman, Jr. | |
| 2,985,970 A * | 5/1961 | McCarthy | A43B 13/00 12/142 R |
| 3,049,120 A * | 8/1962 | Edith | A61F 5/019 602/30 |
| 3,128,763 A | 4/1964 | Langenfeld et al. | |
| 3,299,894 A * | 1/1967 | Charlebois | A61F 13/068 36/140 |
| 4,651,354 A * | 3/1987 | Petrey | A41B 11/004 2/239 |
| 4,745,927 A | 5/1988 | Brock | |
| 5,183,060 A | 2/1993 | Shito | |
| 5,205,071 A * | 4/1993 | Hergenroeder | A43B 5/08 36/106 |

(Continued)

FOREIGN PATENT DOCUMENTS

FR    2235653    7/1973

OTHER PUBLICATIONS www.amazon.com. Gel Toe Socks. Jul. 29, 2014.
www.footsmart.com. FootSmart Gel Lined Compression Toe Separating Socks. Jul. 29, 2014.

Primary Examiner — Katherine Moran
Assistant Examiner — Megan Brandon
(74) Attorney, Agent, or Firm — Joseph E. Maenner; Maenner & Associates, LLC

(57) ABSTRACT

In described embodiments, the invention provides a foot pad having a generally planar substrate having a medial side and a lateral side and an upper surface extending between the medial side and the lateral side. A first toe loop extends upwardly from the medial side. The first toe loop has a first size. A second toe loop extends upwardly from the lateral side. The second toe loop has a second size, smaller than the first size. A third toe loop extends upwardly between the first toe loop and the second toe loop. The third toe loop is smaller than the first toe loop.

18 Claims, 5 Drawing Sheets

(56) References Cited

U.S. PATENT DOCUMENTS

| | | | | |
|---|---|---|---|---|
| 5,533,962 A * | 7/1996 | Peterman | A61F 13/0203 | 602/41 |
| 5,867,838 A * | 2/1999 | Corry | A43B 17/00 | 2/239 |
| 6,018,888 A * | 2/2000 | Wilkenfeld | A43B 3/102 | 36/113 |
| 6,120,473 A * | 9/2000 | Oliverio | A43B 7/142 | 602/41 |
| 7,107,626 B1 * | 9/2006 | Andrews | A41B 11/004 | 2/239 |
| 7,346,935 B1 * | 3/2008 | Patterson | A41B 11/004 | 2/239 |
| 7,559,159 B1 * | 7/2009 | Lundberg | A43B 3/163 | 36/7.1 R |
| 7,682,326 B2 | 3/2010 | Song | | |
| 7,934,325 B2 * | 5/2011 | Sokolowski | A43B 3/126 | 36/113 |
| 8,216,162 B2 * | 7/2012 | Bushby | A43B 7/142 | 36/35 R |
| 8,814,818 B2 * | 8/2014 | Bushby | A61F 5/0111 | 36/35 R |
| 2002/0019602 A1 * | 2/2002 | Geng | A61F 13/02 | 602/42 |
| 2004/0049144 A1 * | 3/2004 | Cea | A61F 13/02 | 602/41 |
| 2004/0055179 A1 * | 3/2004 | Wang | A43B 3/103 | 36/11.5 |
| 2005/0091729 A1 * | 5/2005 | Alley | A41B 11/004 | 2/239 |
| 2005/0177085 A1 | 8/2005 | Green et al. | | |
| 2006/0137224 A1 * | 6/2006 | Song | A43B 5/00 | 36/72 R |
| 2006/0179547 A1 * | 8/2006 | Rosental-Reis | A43B 7/26 | 2/239 |
| 2006/0179549 A1 * | 8/2006 | Huggins | A41B 11/004 | 2/239 |
| 2006/0213087 A1 * | 9/2006 | Gallegos | A43B 3/26 | 36/97 |
| 2006/0265903 A1 * | 11/2006 | Strong | A43B 3/106 | 36/25 R |
| 2006/0288609 A1 * | 12/2006 | Wilkenfeld | A43B 3/105 | 36/8.3 |
| 2007/0006486 A1 * | 1/2007 | Wilkenfeld | A43B 5/12 | 36/8.3 |
| 2009/0090028 A1 * | 4/2009 | Moramarco | A43B 3/102 | 36/96 |
| 2009/0211306 A1 * | 8/2009 | Roberts | D04B 7/34 | 66/186 |
| 2009/0260263 A1 | 10/2009 | Beard | | |
| 2010/0037485 A1 * | 2/2010 | Wu | A43B 3/106 | 36/91 |
| 2010/0043255 A1 * | 2/2010 | Trevino | A43B 3/163 | 36/30 R |
| 2010/0287686 A1 * | 11/2010 | Rosenberg | A41B 11/08 | 2/239 |
| 2011/0047815 A1 * | 3/2011 | Asquith | A43B 17/105 | 36/15 |
| 2011/0072686 A1 * | 3/2011 | Chen | A43B 17/006 | 36/44 |
| 2011/0113530 A1 * | 5/2011 | Ballard | A41B 11/004 | 2/239 |
| 2012/0030866 A1 * | 2/2012 | Snider-Tornetta | A43B 1/0054 | 2/455 |
| 2012/0090077 A1 * | 4/2012 | Brown | A43B 17/14 | 2/239 |
| 2012/0152267 A1 * | 6/2012 | Chang | A43B 3/103 | 132/200 |
| 2012/0255101 A1 * | 10/2012 | Pizzo | A43B 1/0027 | 2/239 |
| 2012/0260533 A1 * | 10/2012 | Nenow | A43B 3/0036 | 36/103 |
| 2012/0285039 A1 * | 11/2012 | Lazaris | A43B 3/102 | 36/11.5 |
| 2013/0091732 A1 * | 4/2013 | Mendoza | A43B 3/0078 | 36/100 |
| 2013/0269213 A1 * | 10/2013 | Gift | A43B 7/26 | 36/101 |
| 2013/0283637 A1 * | 10/2013 | Wilkenfeld | A43B 7/26 | 36/8.3 |
| 2013/0291410 A1 * | 11/2013 | Trauner | A43B 3/10 | 36/30 R |
| 2014/0090273 A1 | 4/2014 | Piontkowski | | |
| 2015/0026868 A1 * | 1/2015 | Sherry | A41B 11/004 | 2/239 |
| 2015/0230551 A1 * | 8/2015 | O'Brien | A43B 17/105 | 36/44 |
| 2015/0282554 A1 * | 10/2015 | Irion | A43B 5/06 | 36/134 |
| 2015/0374094 A1 * | 12/2015 | Gift | A45D 29/22 | 36/94 |

\* cited by examiner

FOOT PAD

BACKGROUND OF THE INVENTION

1. Field of the Invention

The present invention relates to foot pads, and, in particular, to footpads that can be worn with open toed heels or sandals and not be visible.

2. Description of the Related Art

Women's fashion shoes, while attractive, can be tough on a wearer's feet, resulting in blisters. While some attempts have been made to provide coverings over affected parts of the foot in an attempt to reduce the formation of blisters, such attempts fall short with respect to maintaining any semblance of fashion and/or comfort.

It would be beneficial to provide a foot pad that provides the protection against rubbing that forms blisters and the sensitivity of stepping/sliding of the foot against the inside sole of the shoes, which creates friction and basically burns the bottom of the foot, making feet sensitive and hard to walk, while not degrading fashion appearance.

SUMMARY OF THE INVENTION

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter.

In one embodiment, the present invention is a foot pad having a generally planar substrate having a medial side and a lateral side and an upper surface extending between the medial side and the lateral side. A first toe loop extends upwardly from the medial side. The first toe loop has a first size. A second toe loop extends upwardly from the lateral side. The second toe loop has a second size, smaller than the first size. A third toe loop extends upwardly between the first toe loop and the second toe loop. The third toe loop is smaller than the first toe loop.

In an alternative embodiment, the present invention is a foot pad comprising a generally planar substrate having a medial side and a lateral side and an upper surface extending between the medial side and the lateral side. A first toe loop extends anteriorly of the substrate proximal to the medial side. The first toe loop has a first size. A second toe loop extends anteriorly of the substrate proximal to the lateral side. The second toe loop having a second size, smaller than the first size. A third toe loop extends interiorly of the substrate between the first toe loop and the second toe loop. The third toe loop has a third size, smaller than the first size.

BRIEF DESCRIPTION OF THE DRAWINGS

The accompanying drawings, which are incorporated herein and constitute part of this specification, illustrate the presently preferred embodiments of the invention, and, together with the general description given above and the detailed description given below, serve to explain the features of the invention. In the drawings.

DETAILED DESCRIPTION

Figure 1:
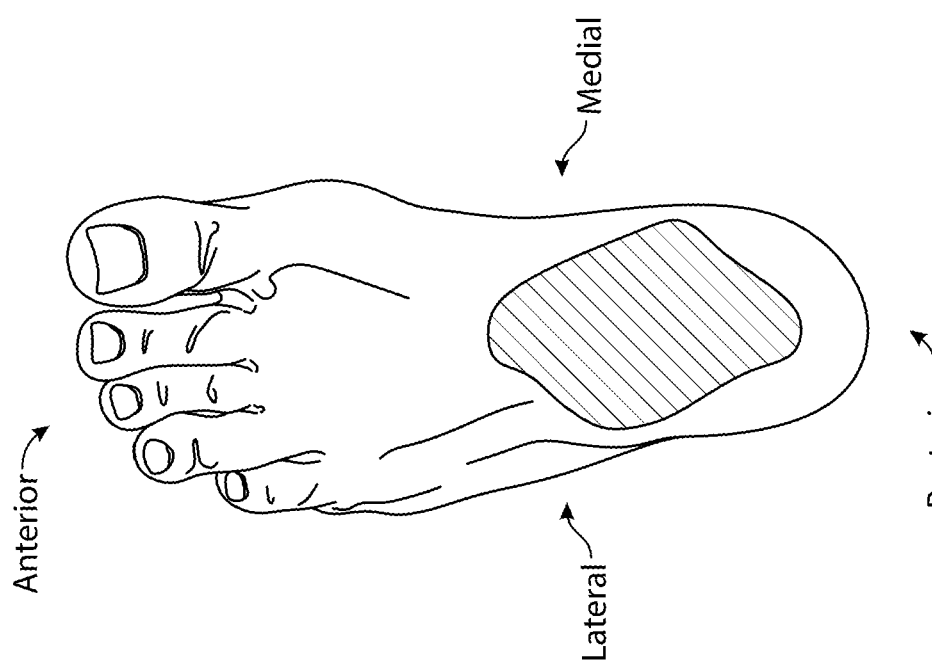
FIG. 1 shows a top plan view of a human left foot and directional connotations used herein.
Figure 3A:
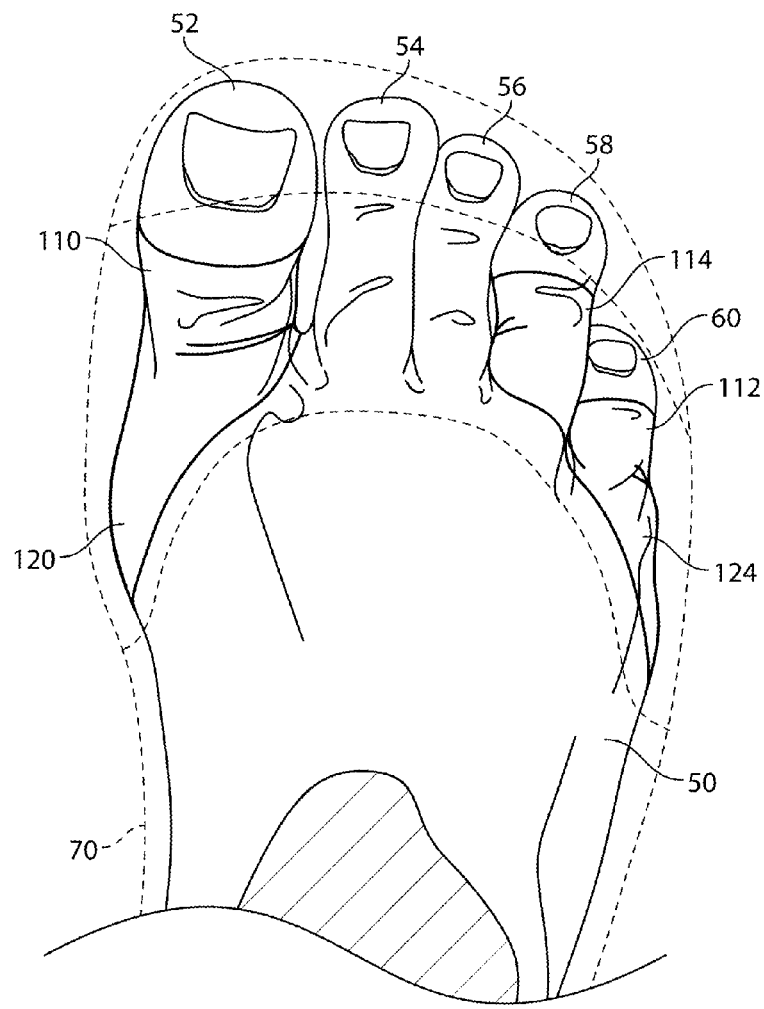
FIG. 3A shows a top plan view of a foot inserted into the foot pad of FIG. 2.
Figure 3B:
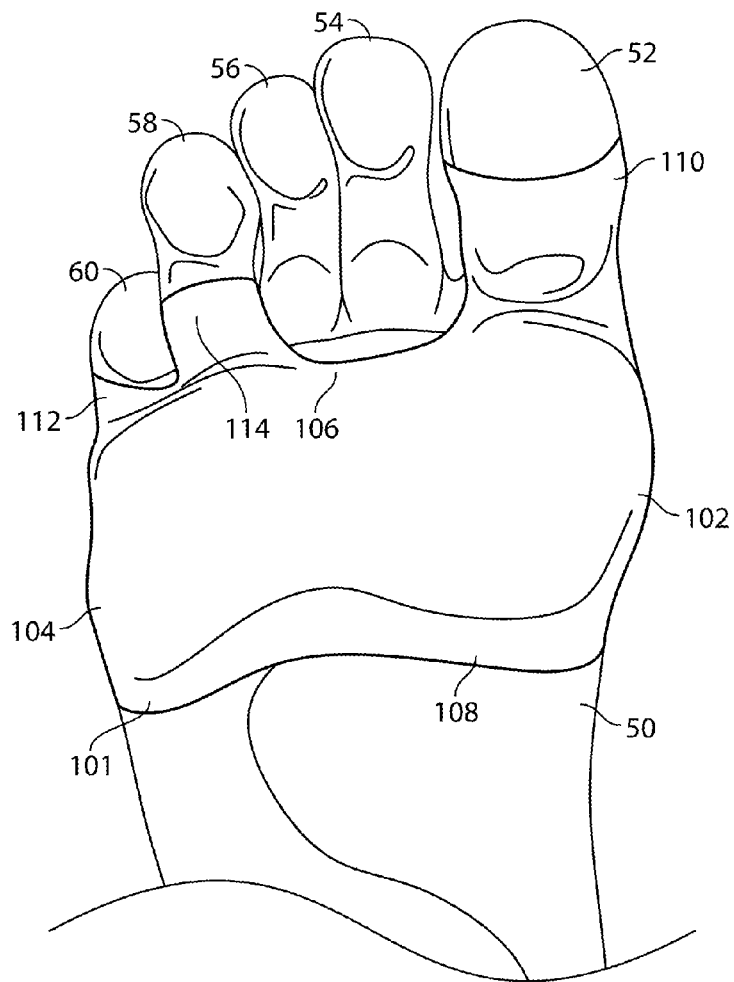
FIG. 3B shows a bottom plan view of a foot inserted into the foot pad of FIG. 2.
Figure 4:
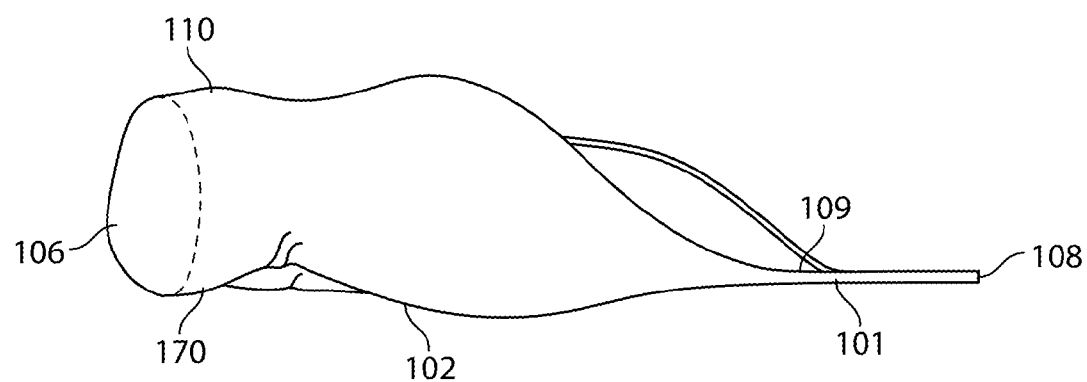
FIG. 4 shows a side elevational view of a medial side of the foot pad of FIG. 2.
Figure 5:
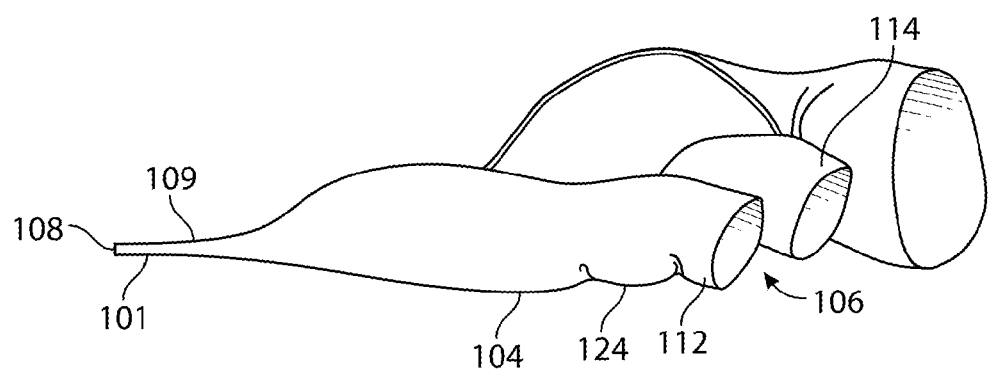
FIG. 5 shows a side elevational view of a lateral side of the foot pad of FIG. 2.

In the drawings, like numerals indicate like elements throughout. Certain terminology is used herein for convenience only and is not to be taken as a limitation on the present invention. The terminology includes the words specifically mentioned, derivatives thereof and words of similar import. As used herein, the term "medial" is defined as a direction toward the arch or first metatarsal on a human foot, the term "lateral" is defined as a direction toward the fifth metatarsal on the human foot; the term "anterior" is defined as a direction toward the toes of the human foot; and the term "posterior" is defined as a direction toward the heel of the human foot. These directions are illustrated in FIG. 1.

The embodiments illustrated below are not intended to be exhaustive or to limit the invention to the precise form disclosed. These embodiments are chosen and described to best explain the principle of the invention and its application and practical use and to enable others skilled in the art to best utilize the invention.

Reference herein to "one embodiment" or "an embodiment" means that a particular feature, structure, or characteristic described in connection with the embodiment can be included in at least one embodiment of the invention. The appearances of the phrase "in one embodiment" in various places in the specification are not necessarily all referring to the same embodiment, nor are separate or alternative embodiments necessarily mutually exclusive of other embodiments. The same applies to the term "implementation."

As used in this application, the word "exemplary" is used herein to mean serving as an example, instance, or illustration. Any aspect or design described herein as "exemplary" is not necessarily to be construed as preferred or advantageous over other aspects or designs. Rather, use of the word exemplary is intended to present concepts in a concrete fashion.

Additionally, the term "or" is intended to mean an inclusive "or" rather than an exclusive "or". That is, unless specified otherwise, or clear from context, "X employs A or B" is intended to mean any of the natural inclusive permutations. That is, if X employs A; X employs B; or X employs both A and B, then "X employs A or B" is satisfied under any of the foregoing instances. In addition, the articles "a" and "an" as used in this application and the appended claims should generally be construed to mean "one or more" unless specified otherwise or clear from context to be directed to a singular form.

Unless explicitly stated otherwise, each numerical value and range should be interpreted as being approximate as if the word "about" or "approximately" preceded the value of the value or range.

The use of figure numbers and/or figure reference labels in the claims is intended to identify one or more possible embodiments of the claimed subject matter in order to facilitate the interpretation of the claims. Such use is not to be construed as necessarily limiting the scope of those claims to the embodiments shown in the corresponding figures.

It should be understood that the steps of the exemplary methods set forth herein are not necessarily required to be performed in the order described, and the order of the steps of such methods should be understood to be merely exemplary. Likewise, additional steps may be included in such methods, and certain steps may be omitted or combined, in methods consistent with various embodiments of the present invention.

Although the elements in the following method claims, if any, are recited in a particular sequence with corresponding labeling, unless the claim recitations otherwise imply a particular sequence for implementing some or all of those elements, those elements are not necessarily intended to be limited to being implemented in that particular sequence.

As used herein in reference to an element and a standard, the term "compatible" means that the element communicates with other elements in a manner wholly or partially specified by the standard, and would be recognized by other elements as sufficiently capable of communicating with the other elements in the manner specified by the standard. The compatible element does not need to operate internally in a manner specified by the standard.

Also for purposes of this description, the terms "couple," "coupling," "coupled," "connect," "connecting," or "connected" refer to any manner known in the art or later developed in which energy is allowed to be transferred between two or more elements, and the interposition of one or more additional elements is contemplated, although not required. Conversely, the terms "directly coupled," "directly connected," etc., imply the absence of such additional elements.

A foot pad 100 according to a first exemplary embodiment of the present invention is shown in FIGS. 2-5. Foot pad 100 is shown for use with a right foot, although those skilled in the art will recognize that a mirror image of foot pad 100 can be used with a left foot. Foot pad 100 is a pliable device into which toes 52-60 of a foot 50 are inserted to protect the toes and anterior part of the foot from rubbing against the inside of a shoe 70 (shown in broken lines in FIG. 3).

Referring back to FIG. 2 and FIGS. 4-5, foot pad 100 includes a generally planar substrate 101 having a medial side 102 and a lateral side 104, distal from medial side 102. Additionally, foot pad includes an anterior portion 106 extending between medial side 102 and lateral side 104, as well as a posterior portion 108 extending posteriorly of anterior portion 106 and extending between medial side 102 and lateral side 104. Substrate 101 also has an upper surface 109 defined by anterior portion 106 and posterior portion 108, between medial side 102 and lateral side 104.

Foot pad 100 also includes a first toe loop 110 having a first size to fit a big toe 52. First toe loop 110 tapers from lateral side 104 toward medial side 102, such that an anterior portion of first toe loop 110 is wider than a posterior portion of first toe loop 110. The tapering of first toe loop 110 provides for a longer portion of toe loop 110 along medial side 102, where a shoe tends to typically be longer, as shown FIGS. 3 and 4.

Second and third toe loops 112, 114 are sized to fit a pinky toe 60, and a fourth toe 58, respectively. Second toe loop 112 is smaller than first toe loop 110 and third toe loop 114 is smaller than first toe loop 110. Optionally, third toe loop 114 can be larger than second toe loop 112.

Figure 2:
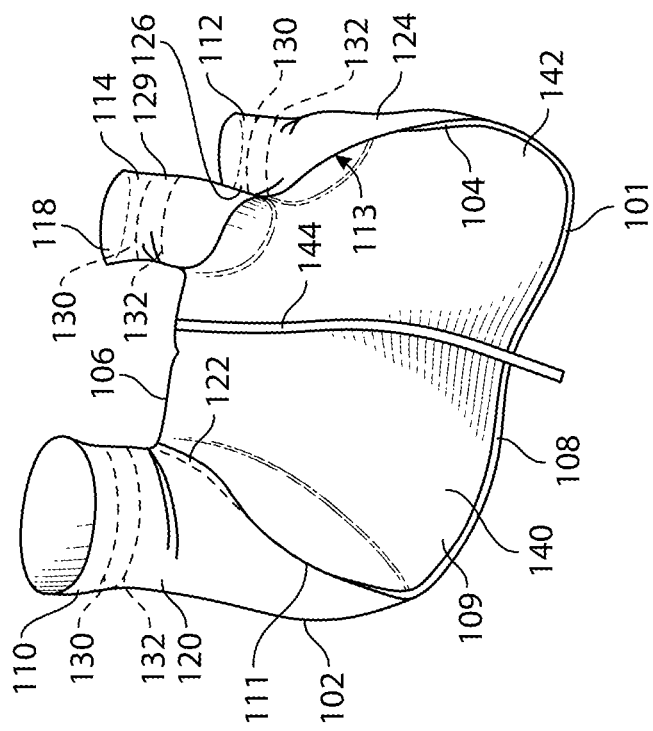
FIG. 2 shows a top plan view of a foot pad according to a first exemplary embodiment of the present invention.
Figure 6:
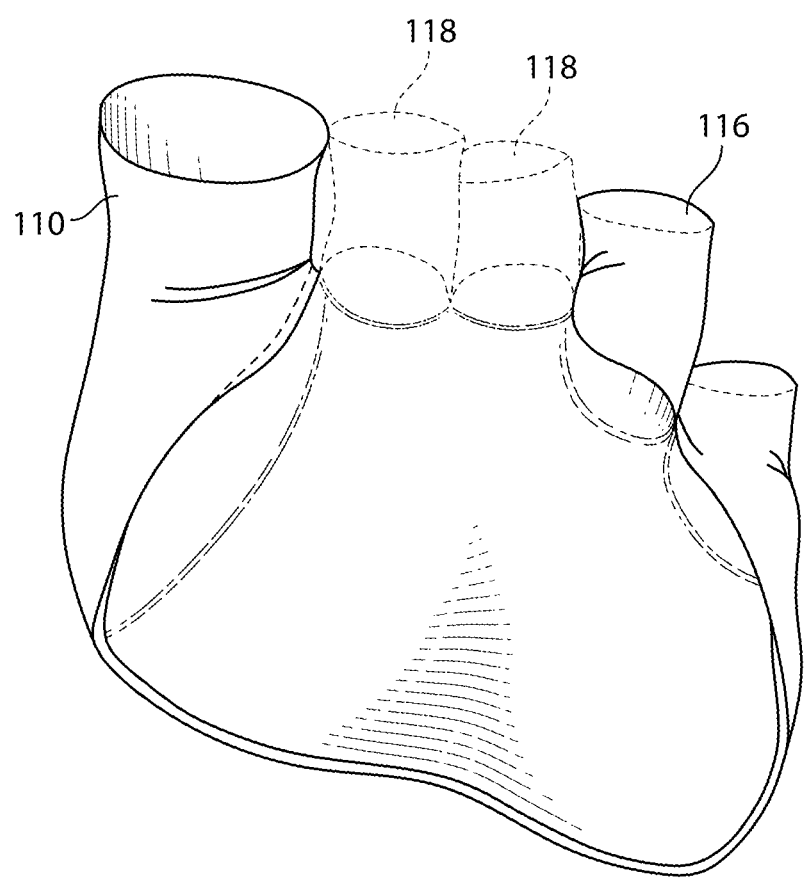
FIG. 6 shows a top plan view of an alternative embodiment of a foot pad according to the present invention.

As shown FIG. 2, only substrate 101 extends between first toe loop 110 and third toe loop 114, resulting in no toe loops for either second or third toes 54, 56, respectively. Alternatively, however, as shown in broken lines in FIG. 6, at least one toe loop 118 can extend between first toe loop 110 and third toe loop 116, allowing at least one of second and third toes 54, 56 to be inserted thereinto.

First toe loop 110 is attached to anterior portion 106 and has a first side 120 extending from medial side 102 and a second side 122 attached to upper surface 109. First toe loop 110 extends anteriorly of substrate 101 proximal to medial side 102. As shown in FIG. 2, an arcuate top wall 111 extends from medial side 102 toward third toe loop 114.

Second toe loop 112 is attached to anterior portion 106 and has a first side 124 extending from lateral side 104 and a second side 126 attached to upper surface 109. Second toe loop 112 extends anteriorly of substrate 101 proximal to lateral side 104. As shown in FIG. 2, second toe loop 112 comprises an arcuate top wall 113 extending from lateral side 104 toward third toe loop 114.

Third toe loop 114 is attached to anterior portion 106 and has a first side 128 extending upwardly from upper surface 109 and a second side 130 extending upwardly from upper surface 109. Third toe loop 114 extends anteriorly of substrate 101 between first toe loop 110 and second toe loop 112.

Optionally, as shown in FIG. 2, at least one of toe loops 110, 112, 114 has at least one perforation 130 extending in a medial-to-lateral direction around the circumference of the toe loop. FIG. 2 shows that each of toe loops 110, 112, 114 has an anterior indicia 130 and a posterior indicia 132. In the event that the user wears shoes with a short toe portion, the user can reduce the length of toe loops 110, 112, 114, as desired by tearing or cutting toe loops 110, 112, 114, along either of indicia 130 or indicia 132 so that toe loops 110, 112, 114 will not extend anteriorly beyond the toe portion of the shoe. Optionally, perforations can be included instead of or in addition to the indicia 130, 132 to facilitate removal of the excess length of toe loops 110, 112, 114.

An adhesive 140 is provided on upper surface 109 of substrate 101. Adhesive 140 can extend along the entirety of upper surface 109. Alternatively, adhesive 140 can extend along only a part of upper surface 109. Adhesive 140 can be used to releasably secure foot pad 100 to the bottom of the user's foot so that foot pad 100 does not slide relative to the foot within the user's shoe.

An adhesive backing 142 is releasably attached to adhesive 140. A pull tab 144 is attached to interior portion of adhesive backing 142, and extends toward a posterior of adhesive backing 142. While pull tab 144 is shown in FIG. 2 as extending posteriorly of adhesive backing 142, those skilled in the art will recognize that pull tab 144 can be shorter, but still long enough for a wearer to be able to reach under her foot and grasp pull tab 144.

To use foot pad 100, user inserts foot 50 into foot pad 100 such that big toe 52, extends through first toe loop 102, fifth toe 60 extends through second toe loop 108, fourth toe 58 extends through third toe loop 106, and second and third toes extend between first toe loop 102 and third toe loop 106. The user then reaches underneath foot 50 and grabs pull tab 144, pulling pull tab 144 posteriorly so that adhesive backing 142 peels off from adhesive 140. When adhesive backing 142 is fully removed from foot pad 100, adhesive backing 142 is discarded. Optionally, adhesive backing 142 can be replaced over adhesive 140 after use.

Foot pad 100 can be constructed from a silicone or other pliable polymer material. Optionally, foot pad 100 can be transparent, translucent, or colored to blend in with the color of the shoe that is being worn. In an exemplary embodiment, foot pad 100 can have a thickness of about 2 mm. In an alternative exemplary embodiment, foot pad 100 can have a thickness of about 1 mm. In still another alternative embodiment, foot pad 100 can have a thickness of about ½ mm. Substrate 101 (except around adhesive 120) can optionally be coated with a skin ointment to provide ointment to the skin of foot 50.

It will be further understood that various changes in the details, materials, and arrangements of the parts which have been described and illustrated in order to explain the nature of this invention may be made by those skilled in the art without departing from the scope of the invention as expressed in the following claims.

What is claimed is:

1. A foot pad comprising: a generally planar substrate having a medial side, a lateral side, an anterior portion, and a posterior portion; an upper surface of the substrate extending between the medial side, the lateral side, the anterior portion, and the posterior portion; a first toe loop extending upwardly from the medial side with a first edge, the first toe loop having a first size and being adapted to fit a big toe; a second toe loop extending upwardly from the lateral side with a second edge, the second toe loop having a second size and being adapted to fit a pinky toe, smaller than the first size; a third toe loop extending upwardly between the first toe loop and the second toe loop, the third toe loop having a third edge, and the third toe loop being smaller than the first toe loop and being adapted sized to fit a fourth toe; wherein the substrate further comprises the anterior portion having an anterior edge and the posterior portion having a posterior edge; and wherein the first edge, the second edge, the third edge, the anterior edge, and the posterior edge together form a continuous edge.

2. The foot pad according to claim 1, wherein the third toe loop is larger than the second toe loop.

3. The foot pad according to claim 1, wherein the first toe loop has a first side extending from the medial side and a second side attached to the upper surface.

4. The foot pad according to claim 1, wherein the second toe loop has a first side extending from the lateral side and a second side attached to the upper surface.

5. The foot pad according to claim 1, wherein the third toe loop has a first side extending upwardly from the upper surface and a second side extending upwardly from the upper surface.

6. The foot pad according to claim 1, wherein the first, second, and third toe loops are attached to the anterior portion.

7. The foot pad according to claim 1, further comprising an adhesive on the upper surface, and wherein the foot pad further comprises an adhesive backing releasably attached to the adhesive.

8. The foot pad according to claim 7, wherein the adhesive backing comprises a pull tab attached to an anterior portion of the adhesive backing and extending toward a posterior portion of the cover.

9. The foot pad according to claim 1, wherein the first toe loop tapers from the lateral side toward the medial side.

10. The foot pad according to claim 1, further comprising at least one toe loop extending between the first toe loop and the third toe loop.

11. The foot pad according to claim 1, wherein at least one of the toe loops has at least one indicia extending in a medial-to-lateral direction around the circumference of the at least one of the toe loops.

12. A foot pad comprising: a generally planar substrate having a medial side, a lateral side, an anterior portion, and a posterior portion; an upper surface of the substrate extending between the medial side, the lateral side, the anterior portion, and the posterior portion; a first toe loop extending anteriorly of the substrate proximal to the medial side and having a first edge, the first toe loop having a first size; a second toe loop extending anteriorly of the substrate proximal to the lateral side and having a second edge, the second toe loop having a second size, smaller than the first size; and a third toe loop extending anteriorly of the substrate between the first toe loop and the second toe loop, the third toe loop having a third edge, and the third toe loop having a third size, smaller than the first size; wherein the substrate further comprises the anterior portion having an anterior edge and the posterior portion having a posterior edge; and wherein the first edge, the second edge, the third edge, the anterior edge, and the posterior edge together form a continuous edge.

13. The foot pad according to claim 12, wherein the first toe loop comprises an arcuate top wall extending from the medial side toward the third toe loop.

14. The foot pad according to claim 12, wherein the second toe loop comprises an arcuate top wall extending from the lateral side toward the third toe loop.

15. The foot pad according to claim 12, further comprising at least one toe loop extending anteriorly of the substrate between the first toe loop and the third toe loop.

16. The foot pad according to claim 12, wherein at least one of the toe loops has at least one perforation extending in a medial-to-lateral direction around the circumference of the at least one of the toe loops.

17. The foot pad according to claim 12, further comprising an adhesive on the substrate.

18. A foot pad comprising: a generally planar substrate having a medial side, a lateral side, an anterior portion, and a posterior portion; an upper surface of the substrate extending between the medial side, the lateral side, the anterior portion, and the posterior portion; a first toe loop extending anteriorly of the substrate and having a first edge, the first toe loop having a first size adapted to fit a big toe; a second toe loop extending anteriorly of the substrate and having a second edge, the second toe loop having a second size adapted to fit a pinky toe, smaller than the first size; a third toe loop extending anteriorly of the substrate between the first toe loop and the second toe loop, the third toe loop having a third edge, and the third toe loop having a size adapted to fit a fourth toe; wherein the substrate further comprises the anterior portion having an anterior edge and the posterior portion having a posterior edge; and wherein the first edge, the second edge, the third edge, the anterior edge, and the posterior edge together form a continuous edge.

* * * * *